(12) United States Patent
Suenaga et al.

(10) Patent No.: US 8,329,153 B2
(45) Date of Patent: Dec. 11, 2012

(54) COSMETIC PRODUCT

(75) Inventors: Koji Suenaga, Tokyo (JP); Toshihisa Nasa, Tokyo (JP)

(73) Assignee: Momentive Performance Materials Japan LLC, Tokyo (JP)

( * ) Notice: Subject to any disclaimer, the term of this patent is extended or adjusted under 35 U.S.C. 154(b) by 0 days.

(21) Appl. No.: 12/736,661

(22) PCT Filed: Apr. 30, 2009

(86) PCT No.: PCT/JP2009/001948
§ 371 (c)(1),
(2), (4) Date: Oct. 27, 2010

(87) PCT Pub. No.: WO2009/136486
PCT Pub. Date: Nov. 12, 2009

(65) Prior Publication Data
US 2011/0040062 A1    Feb. 17, 2011

(30) Foreign Application Priority Data
May 8, 2008  (JP) .................................. 2008-122505

(51) Int. Cl.
*C08G 77/04* (2006.01)
(52) U.S. Cl. .................. 424/70.121; 424/70.7; 424/401; 528/10
(58) Field of Classification Search .................. 424/401, 424/70.121, 70.7; 528/10
See application file for complete search history.

(56) References Cited

U.S. PATENT DOCUMENTS

| | | | | |
|---|---|---|---|---|
| 4,670,299 A | * | 6/1987 | Fukuyama et al. | 427/99.3 |
| 4,988,514 A | * | 1/1991 | Fukuyama et al. | 428/447 |
| 5,676,938 A | * | 10/1997 | Kimura et al. | 424/78.03 |
| 7,482,419 B2 | * | 1/2009 | Caprasse et al. | 528/15 |
| 2006/0008411 A1 | * | 1/2006 | Alt et al. | 423/566.2 |
| 2007/0149703 A1 | * | 6/2007 | Caprasse et al. | 524/588 |

FOREIGN PATENT DOCUMENTS

| | | | |
|---|---|---|---|
| EP | 590 192 | * | 6/1994 |
| JP | 61-065808 | | 4/1986 |
| JP | 61-158910 | | 7/1986 |
| JP | 62-234012 | | 10/1987 |
| JP | 62-298511 | | 12/1987 |
| JP | 02-042008 | | 2/1990 |
| JP | 4-312511 | | 11/1992 |
| JP | 2009-155224 | | 7/2009 |

* cited by examiner

*Primary Examiner* — Margaret Moore
(74) *Attorney, Agent, or Firm* — Flynn, Thiel, Boutell & Tanis, P.C.

(57) ABSTRACT

The present invention provides cosmetic products, such as makeup cosmetics and skin care cosmetics, which have a good water-proof and perspiration resistance and an excellent use feel, such as spreadability, at the time of application and long-wearing capabilities. Specifically, a cosmetic product containing a silicone resin, composed of (A) and (B) described below:

$R_3SiO_{1/2}$ unit    (A)

$RSiO_{3/2}$ unit    (B)

at a proportion of (A):(B) being 1:1 to 1:7 and having a softening point of 50 to 110° C., wherein R represents a substituted or unsubstituted monovalent hydrocarbon group.

10 Claims, No Drawings

COSMETIC PRODUCT

TECHNICAL FIELD

The present invention relates to cosmetic products and, more specifically, cosmetic products having a good water- and perspiration-resistance, an excellent feel in use, such as spreadability at the time of application, and long-wearing capability.

BACKGROUND ART

Recently, responding to a growing diverse demand for makeup cosmetic products, their product forms are wide-ranging not only in constituent items, such as lip rouge, foundation, face powder or manicure, but also in the elements of form such as liquid, powder, solid or emulsion to subdivide these items.

In particular, in addition to better water- and perspiration-resistance (sebum resistance) than the conventional ones, recent cosmetic products demand a good feeling at the time of application and various physical and chemical properties such as friction resistance.

A method using a silicone resin having a coat-forming ability is suggested in order to satisfy such demands. The application of such a resin for cosmetic product purposes is widely known, for example, a cosmetic product made by blending a silicone resin composed of $RnSiO_{(4-n/2)}$ units with a volatile hydrocarbon oil or volatile silicone oil (see JP-A 61-158910); a cosmetic product containing a mixture of a silicone resin composed of $RSiO_{3/2}$ units, $SiO_2$ units and $R_2SiO$ units and a silicone resin composed of $RSiO_{3/2}$ units and $SiO_2$ units (see JP-A 2-42008); a skin care cosmetic product containing a resin composed of $R_3SiO_{1/2}$ units and $SiO_2$ units and a volatile silicone oil (see JP-A 61-65808); a sunscreen cosmetic product made by blending a resin composed of $SiO_2$ units, $RSiO_{3/2}$ units and $R_2SiO$ units with a volatile silicone oil (see JP-A 62-234012); and a cosmetic product containing a silicone resin composed of $R_3SiO_{1/2}$ units and $SiO_2$ units and also $R_2SiO$ units and/or $RSiO_{3/2}$ units or that further contain a volatile silicone oil or powder (see JP-A 62-298511). Further, the application of a silicone resin wherein an organosilsesquioxane which is composed of $RSiO_{3/2}$ units and contains a silanol group is sequestered by a triorganosilyl group to a cosmetic product is a widely known technology (see JP-A 4-3511).

DISCLOSURE OF THE INVENTION

However, many of the well known technologies as described above make use of a silicone resin having a $SiO_2$ unit and, thus, the hardness of the coats tends to provide a taut feeling and, also, the fragility of the coats leads to the loss of the coats around the eyes and mouth, which creates problems of a poor lasting capability of a makeup coat. Furthermore, a silicone resin described in JP-A 4-312511 has been improved in the hardness and fragility of the coats but, as of now, the softness of the coats is not enough and, thus, improvements have been required in these points.

The present invention relates to cosmetic products wherein the problems mentioned above have been solved, aims to provide cosmetic products such as makeup cosmetic products and skin care cosmetic products having good water- and perspiration-resistance and excellent feel in use, such as spreadability at the time of application, and a long-wearing capability.

The present inventors have strenuously studied to achieve the aims described above and found that a useful cosmetic product can be obtained by blending a particular silicone resin composed of $R_3SiO_{1/2}$ units and $RSiO_{3/2}$ units at a particular proportion, and thus have completed the present invention.

Thus, the present invention is a cosmetic product, containing a silicone resin, containing (A) and (B) described below:

$R_3SiO_{1/2}$ unit  (A)

$RSiO_{3/2}$ unit  (B)

at a proportion of (A):(B) being 1:1 to 1:7 and having a softening point of 50 to 110° C., wherein R represents a substituted or unsubstituted monovalent hydrocarbon group.

The present invention is a cosmetic composition containing the silicone resin described above and other cosmetic components or use of the silicone resin described above as a cosmetic product.

The cosmetic product of the present invention has a good spreadability and, when it is applied to the skin, it provides not an icky but a refreshing feeling. It has good use properties in that make up deterioration caused by perspiration doesn't occur and further in that the cosmetic product hardly washes away by water and so on, and it also has a good stability over time. When used as a skin care cosmetic product, the cosmetic product of the present invention provides a plain and no sticky feeling and a good water-proofness caused by an excellent water repellency. Furthermore, when used as a makeup cosmetic product, it provides a good and even spreadability, excellent long-wearing capability caused by its excellent water repellency, water-proofness and the like, a good appearance resulting from an excellent luster and coloring of pigment, smooth embrocation and so on.

DETAILED DESCRIPTION OF THE INVENTION

In the silicone resin used in the present invention, Rs in (A) and (B) respectively represent substituted or unsubstituted monovalent hydrocarbon groups which are identical to or different from each other. Examples of R are alkyl groups such as methyl, ethyl, propyl or butyl groups; alkenyl groups such as vinyl or allyl groups; aryl groups such as phenyl or tolyl groups; cycloalkyl groups such as cyclohexyl or cyclooctyl groups; or groups wherein a hydrogen atom bonded to a carbon atom in those described above is substituted by a halogen atom, cyano group, amino group etc., for example, chloromethyl, 3,3,3-trifluoropropyl, cyanomethyl, γ-aminopropyl and N-(β-aminoethyl)-γ-aminopropyl groups and the like. In terms of the ease of synthesis and ease of availability of raw materials, methyl, ethyl and phenyl groups are preferred, and in terms of water repellency, methyl, 3,3,3-trifluoropropyl and phenyl groups are preferred.

The proportion of the (A) $R_3SiO_{1/2}$ unit and (B) $RSiO_{3/2}$ unit is required to be from 1:1 to 1:7. The proportion of the (A) $R_3SiO_{1/2}$ unit and (B) $RSiO_{3/2}$ unit is preferably from 1:2 to 1:6 and, more preferably, from 1:3 to 1:6. If the proportion of (A) $R_3SiO_{1/2}$ unit and (B) $RSiO_{3/2}$ unit is less than 1:1, a coating performance sufficient for cosmetic product purposes can be hardly obtained and, on the other hand, if the proportion exceeds 1:7, the coating becomes hard, resulting in a poor long-wearing capability. Therefore the effects of the present invention cannot be sufficiently obtained in both cases.

The silicone resin of the present invention has a solid form, having a thermoplasticity at a softening point of 50 to 110° C. The preferable softening point is within the range of 60 to 100° C. If it has a softening point less than 50° C., the coat becomes icky, which is unfavorable. Further, silicone resin having a softening point of more than 110° C. provides coat itself with poor spreadability and not enough softness, and when blended in a cosmetic product, it cannot provide a sufficient long-wearing capability, which is unfavorable.

Moreover, the molecular weight is preferably from 5,000 to 500,000 because a soft and well spreadable coat with no icky feeling can be obtained at room temperature. More preferably, the molecular weight is from 7,000 to 400,000. If the molecular weight is less than 5,000, the coat becomes icky and unfavorable. Furthermore, a silicone resin having a molecular weight of more than 500,000 provides the coat itself with a poor spreadability and not enough softness, which is unfavorable. Here, the molecular weight means a weight-average molecular weight as measured by GPC in terms of polystyrene and can be measured by a commercially available apparatus.

Further, such a silicone resin usually contains approximately 1 to 5 wt % of a silanol group, and often exhibits a thermosetting property by heating at a high temperature for a long time, thus it has an excellent stability and a flexible coat-forming property. Further, when also used in cosmetic products, it can provide good properties, and thus the use of preferably a silicone resin containing an amount of 0.01 to 0.5 wt % of silanol group is preferable.

Such a silicone resin is produced by the first step of performing a hydrolysis and condensation reaction of an alkoxysilane represented by the formula (C) below and the second step of performing silylation with a chlorosilane represented by the formula (D):

RSi(OR')$_3$                               (C)

R$_3$SiCl                                    (D)

wherein R represents a substituted or unsubstituted monovalent hydrocarbon group and R' represents a substituted or unsubstituted hydrocarbon group having 1 to 6 carbon atoms.

Here, R represents a substituted or unsubstituted monovalent hydrocarbon group, and one identical to the monovalent hydrocarbon group described above can be used. Examples of R' include alkyl groups such as methyl, ethyl, propyl, isopropyl, butyl, pentyl or hexyl groups; cycloalkyl groups such as a cyclohexyl group; or groups wherein a hydrogen atom bonded to a carbon atom in those described above is substituted by a halogen atom and the like, for example, chloromethyl, 3,3,3-trifluoropropyl groups and the like; and a substituted or unsubstituted hydrocarbon group having 1 to 6 carbon atoms.

Meanwhile, the hydrolysis and condensation reaction of an alkoxysilane having the formula (C) is generally performed under an acidic condition. The acid used there can be inorganic acids such as sulfuric acid, hydrochloric acid, nitric acid or phosphoric acid; and organic acids such as formic acid, acetic acid or p-toluenesulfonic acid. These acids may be directly added to alkoxysilane before the initiation of hydrolysis reaction, or they may be added in advance to the water for use in hydrolysis reaction and used in a state of an acidic aqueous solution. Further, a method for converting chlorosilanes such as trimethylchlorosilane, methyltrichlorosilane, triphenylchlorosilane or phenyltrichlorosilane into hydrochloric acid by adding these chlorosilanes in the presence of alkoxysilane and alcohol such as methanol, ethanol, propanol, isopropanol or butanes through the use of exchange reaction between these chlorosilanes and these alcohols can be also used. The acid is preferably added so that the amount of the acid is from 0.1 to 3 wt % to alkoxysilane, more preferably from 0.3 to 2.5 wt %. If the amount of the acid is 0.1% or less, the hydrolysis and condensation reaction cannot progress sufficiently, and if it exceeds 3 wt %, the reaction progresses too fast, which results in making the control of the molecular weight difficult. In terms of the amount of water to be used for the hydrolysis, the stoichiometric amount needed for hydrolyzing the alkoxysilane is enough, but a large amount of water is also acceptable. Furthermore, the hydrolysis and condensation reaction is performed for 1 to 24 hours at the temperature of 0 to 100° C. The reaction is preferably performed for 1 to 15 hours at 10 to 90° C., and more preferably for 1 to 10 hours at 25 to 80° C. In this way, the silicone resin of the present invention having a softening point of 50 to 110° C. and a molecular weight of 5,000 to 500,000 can be produced by appropriately selecting the concentration of the acid described above and the temperature and period of the hydrolysis and condensation reaction.

Moreover, various organic solvents may be used in the hydrolysis and condensation reaction. Examples of such organic solvents include hydrocarbon-based solvents such as toluene, xylene, hexane, isoparaffin, industrial gasoline, mineral spirits or kerosene; ether-based solvents such as tetrahydrofuran or dioxane; and chlorinated hydrocarbon-based solvents such as dichloromethane or dichloroethane. Meanwhile, the amount of these organic solvents to be used is preferably 20 wt % or less to the alkoxysilane. If it exceeds 20 wt %, the molecular weight of silicone resin obtained becomes relatively small and, as a result, it becomes difficult to obtain a soft and well spreadable coat.

The silylation reaction is performed by using a chlorosilane represented by the formula (D). The amount of chlorosilane to be used is from 0.1 to 1 mol relative to 1 mol of alkoxysilane used in hydrolysis. Furthermore, if the amount is less than 0.1 mol, silylation becomes insufficient, which causes gelation during the reaction or deteriorating the heat stability of the silicone resin obtained. If the amount exceeds 1 mol, the softening point and the molecular weight of the silicone resin obtained become unfavorably lowered, and thus it becomes difficult to obtain the silicone resin of the present invention in any event.

Meanwhile, the silylation described above is performed for 1 to 24 hours at 0 to 100° C. Preferably, it is conducted for 1 to 15 hours at 10 to 90° C., and more preferably for 1 to 10 hours at 25 to 80° C. This silylation is preferably performed in an organic solvent to prevent an excessive condensation reaction or gelation. Such organic solvents include hydrocarbon-based solvents such as toluene, xylene, hexane, isoparaffins, industrial gasolines, mineral spirits or kerosene; ether-based solvents such as tetrahydrofuran or dioxane; and chlorinated hydrocarbon-based solvents such as dichloromethane or dichloroethane. These organic solvents are preferably added together with chlorosilane. Meanwhile, the amount of these organic solvents to be used is preferably 10 to 100 parts by weight relative to trialkoxysilane, but is not restricted in particular.

As just described, the silicone resin of the present invention is a thermoplastic solid-state resin, and soluble in organic solvents and capable of being emulsified by using an emulsifier and the like. Therefore, the silicone resin of the present invention is different from generally known hardened silicone resins which are known as silicone resin hardeners, not having thermoplasticity and being insoluble in solvents.

Cosmetic products, such as makeup cosmetic products, for example, foundation, pressed powder, eyeshadow, nail enamel, lip rouge and mascara and skin care cosmetic products can be obtained by blending 0.1 to 100 parts by weight of the silicone resin thus obtained.

For the cosmetic product of the present invention, in addition to the silicone resin described above, which is an essential component, raw materials usually used in cosmetic products are selected and blended appropriately depending on the type of a cosmetic product. For example, the following can be blended: various hydrocarbons such as squalane, liquid paraffins, isoparaffins, vaseline, microcrystalline wax, ozokerite, ceresin, myristic acid, palmitic acid, stearic acid, oleic acid, isostearic acid, cetyl alcohol, stearyl alcohol, hexadecyl alcohol, oleyl alcohol, cetyl-2-ethylhexanoate, 2-ethylhexylpalmitate, 2-octyldodecyl myristate, 2-octyldodecyl gum ester, neopentyl glycol-2-ethylhex glycol, isooctylic acid triglyceride, 2-octyldodecyl oleate, isopropyl myristate, isopropyl palmitate, isostearic acid triglyceride, palm oil fatty acid triglyceride, olive oil, avocado oil, beeswax, myristyl myristate, mink oil or lanolin; oils such as higher fatty acids, fats and oils, esters, higher alcohol, waxes, or silicone oils; organic solvents such as acetone, toluene, butyl acetate or ethyl acetate; resins such as alkyd resins, acryl resins or urea resins; plasticizers such as camphor or acetyl tributyl citrate; ultraviolet absorbers, antioxidants, antiseptics, surfactants, moisturizers, flavorants, water, alcohols, thickeners and so on. Further, as a powder for use in cosmetic products, the following can be used: for example, inorganic powders such as talc, kaolin, sericite, muscovite, synthesized mica, phlogopite, lepidolite, biotite, lithia mica, vermiculite, magnesium carbonate, calcium carbonate, diatomaceous earth, magnesium silicate, calcium silicate, aluminum silicate, barium silicate, barium sulfate, strontium silicate, tungsten acid metal salts, silica, hydroxyapatite, zeolite, boron nitride or ceramic powder; organic powders such as nylon powder, polyethylene powder, benzoguanamine powder, tetrafluoroethylene powder, distyrene-benzene-pinhole polymer powder or microcrystaliine cellulose; inorganic white pigments such as silicone rubber, silicone resin powder, titanium oxide or zinc oxide; inorganic red pigments such as iron oxide (colcothar) or iron titanate; inorganic brown pigments such as γ-iron oxide; inorganic yellow pigments such as yellow iron oxide or loess; inorganic black pigments such as black iron oxide or carbon black; inorganic purple pigments such as mango violet or cobalt violet; inorganic green pigments such as chromium oxide, chromium hydroxide or cobalt titanate; inorganic blue pigments such as ultramarine or iron blue; pearl pigments such as titanium oxide-coated mica, titanium oxide-coated bismuth oxychloride, bismuth oxychloride, titanium oxide-coated talc, argentine or colored titanium oxide-coated mica; metal powder pigments such as aluminum powder or copper powder; organic pigments such as Pigment Red 201, Pigment Red 202, Pigment Red 204, Pigment Red 205, Pigment Red 220, Pigment Red 226, Pigment Red 228, Pigment Red 405, Pigment Orange 203, Pigment Orange 204, Pigment Yellow 205, Pigment Yellow 401 or Pigment Blue 404; organic pigments such as Pigment Red 3, Pigment Red 104, Pigment Red 106, Pigment Red 227, Pigment Red 203, Pigment Red 401, Pigment Red 505, Pigment Orange 205, Pigment Yellow 4, Pigment Yellow 5, Pigment Yellow 202, Pigment Yellow 203, Pigment Green 3 or Pigment Blue 1 of zirconium, barium or aluminum lake; and natural pigments such as chlorophyll or p-Carotene, but are not limited to them.

EXAMPLES

The following description explains the invention with respect to Examples. Part in Examples indicates part by weight and % indicates weight percent. Further, a weight-average molecular weight indicates the one measured by using GPC (LC Solution, manufactured by Shimadzu.co.jp) (in terms of polystyrene); a softening point indicates the value measured in accordance with Ring and Ball Softening Point Test of JIS C2104; a molar ratio of M unit and T unit is the value calculated by the measurement of $^{29}$Si-NMR using NMR (ARX400, manufactured by Bruker BioSpin K. K.); and a silanol group content was obtained by measuring the amount of water generated at the time of heating the silicone resin for 2 hours at 300° C. using Coulometric Titration-based water content-measuring equipment type CA-06 (manufactured by Mitsubishi Chemical Industries Ltd.) and calculating the amount by using the formula described below.

$$A\ silanol\ group\ content\ (\%) = \frac{\text{The amount of water generated} \times 34/18}{\text{Silicone resin weight}} \times 100$$

Preparation Example 1

1763 (8 mols) parts of methyltriisopropoxysilane and 176 parts of isopropanol were placed in a flask, and methyltrichlorosilane was added while stirring to make a hydrochloric acid concentration of 1.1%. Then, 860 parts of water was added for 1 hour at 40 to 70° C. and stirring was continued for 1 hour at 70 to 80° C. to perform a hydrolysis and condensation reaction of the silane. Then, the mixture of 217 parts (2 mols) of trimethylchlorosilane and 700 parts of isoparaffin-type hydrocarbon (having 9 to 12 carbon atoms) was added for 1 hour at 70 to 80° C. for trimethylsilylation. After the dropwise addition, stirring was conducted for another 1 hour at the same temperature, and then 430 parts of water was added for separation. The organic layer after the separation was washed with water to remove hydrochloric acid and, further, an isoparaffin-type hydrocarbon was distilled off under a reduced pressure, thus obtaining silicone resin A-1 having a molecular weight of 27,000 and a softening point of 80° C. Meanwhile, the molar ratio of $(CH_3)_3SiO_{1/2}$ unit {M unit} of A-1 to $CH_3SiO_{3/2}$ unit (T unit) was 1:5.8. Further, the silanol group content was 0.3%.

Preparation Example 2

Silicone resin A-2 having a weight-average molecular weight of 8,000, a softening point of 50° C., a molar ratio of M unit:T unit of 1:4.7 and a silanol group content of 0.4% was obtained in the same manner as in Preparation Example 1 except for using a hydrochloric acid concentration of 0.7%, 326 parts (3 mols) of trimethylchlorosilane, and 700 parts of isododecane instead of 700 parts of the isoparaffin-type hydrocarbon (having 9 to 12 carbon atoms).

Preparation Example 3

1763 (8 mols) parts of methyltriisopropoxysilane, 176 parts of isopropanol and 200 parts of an isoparaffin-type hydrocarbon (having 9 to 12 carbon atoms) were placed in a flask and methyltrichlorosilane were added while stirring to make the hydrochloric acid concentration of 1.5%. Then, 860 parts of water was added for 1 hour at 40 to 70° C. to perform hydrolysis of the silane. After the dropwise addition, stirring was conducted for 3 hours at 70 to 80° C., and then the mixture of 163 parts (1.5 mols) of trimethylchlorosilane and 500 parts of isoparaffin-type hydrocarbon (having 9 to 12 carbon atoms) was added for 1 hour at 70 to 80° C. to perform trimethylsilylation. After the dropwise addition, stirring was conducted for another 2 hours at the same temperature, and then 430 parts of water was added for separation. The organic layer after the separation was washed with water to remove hydrochloric acid, and the isoparaffin-type hydrocarbon was distilled off under a reduced pressure to obtain silicone resin A-3 having (a molecular weight of) 172,000, a softening point of 102° C., a molar ratio of M unit:T unit of 1:5.5 and a silanol group content of 0.2%.

Preparation Example 4

Silicone resin A-4 having a weight-average molecular weight of 31,000 and a softening point of 58° C., a molar ratio of M unit:T unit of 1:5.7 and a silanol group content of 0.4% was obtained in the same manner as in Preparation Example 1 except for using a hydrochloric acid concentration of 1.2%, the silane 109 parts (1 mol) instead of 217 parts (2 mols) of trimethylchlorosilane, and 3,3,3-trifluoropropylchlorosilane 191 parts (1 mol).

Preparation Example 5

As a Comparative Example, silicone resin B-1 having a weight-average molecular weight of 6,000, a softening point of 36° C., a molar ratio of M unit:T unit of 1:4.1 and a silanol group content of 0.5% was obtained in the same manner as in Preparation Example 1 except for making the hydrochloric acid concentration 0.5%.

Preparation Example 6

For a Comparative Example, 220 parts (1 mol) of methyltriisopropoxysilane, 150 parts of toluene and 22 parts of isopropanol were placed in a flask and methyltrichlorosilane was added so as to make a hydrochloric acid concentration of 1.2%. Then 108 parts of water was added for 20 minutes to perform hydrolysis of the silane. Stirring was stopped 40 minutes after the dropwise addition, then the organic layer obtained after the separation was washed with water to remove hydrochloric acid, and then toluene was removed under a reduced pressure to prepare methylpolysilsesquioxane P-1 having a molecular weight of 15,000 and a softening point of 115° C. Next, 100 parts of said silsesquioxane, 200 parts of toluene, 10 parts (0.09 mol) of trimethylchlorosilane and 50 parts (0.3 mol) of hexamethyldisilazane were placed in a flask for heat stirring. After the heat stirring for 2 hours at toluene's reflux temperature, ammonia, hydrochloric acid or their salts generated by the reaction was removed by washing with water and then toluene was distilled off under reduced pressure, thereby obtaining a trimethylsilylated silicone resin B-2 having a weight-average molecular weight of 15,000 and a softening point of 94° C., a molar ratio of M unit:T unit of 1:9.6 and a silanol group content of 0.3%.

Preparation Example 7

As a Comparative Example, trimethylsilylated silicone resin B-3 having a weight-average molecular weight of 9,000 and a softening point of 73° C., a molar ratio of M unit:T unit of 1:7.9 and a silanol group content of 0.3% was obtained in the same manner as in Preparation Example 5 after preparing methylpolysilsesquioxane P-2 having a weight-average molecular weight of 9,000 and a softening point of 90° C. in the same manner as in Preparation Example 5 except for making the hydrochloric acid concentration 0.8%.

Preparation Example 8

For a Comparative Example, 1761 parts (8 mols) of methyltriisopropoxysilane, 176 parts of isopropanol, 217 parts (2 mols) of trimethylchlorosilane, and 700 parts of isoparaffin-type hydrocarbon (having 9 to 12 carbon atoms) were placed in a flask followed by starting stirring. Then, 860 parts of water was added for 30 minutes to perform hydrolysis of the silane. After the dropwise addition, the resultant solution was stirred for 1 hour at 70 to 80° C. and then, 430 parts of water for separation was added. The organic layer after the separation was washed with water to remove hydrochloric acid and, further, an isoparaffin-type hydrocarbon was distilled off under a reduced pressure. The substance obtained was oily at 25° C.

Preparation Example 8

For a Comparative Example, 1761 parts (8 mols) of methyltriisopropoxysilane, 176 parts of isopropanol and 700 parts of isoparaffin-type hydrocarbon (having 9 to 12 carbon atoms) were placed in a flask and added to methyltrichlorosilane while stirring to make a hydrochloric acid concentration of 1.1%. Then, 860 parts of water was added for 30 minutes to perform hydrolysis of the silane. When stirring was conducted for 1 hour at 70 to 80° C. after the dropwise addition, a gel-like deposition appeared and the desired silicone resin was not obtained.

(Checking Coat Properties)

Silicone resin A-1 obtained in Preparation Example 1 was dissolved in decamethylcyclopentasiloxane so as to make a concentration 50%. 0.5 g of the resultant solution was uniformly applied to the surface of an artificial leather measuring 5 an long×10 an wide (SUPPLALE manufactured by Idemitsu Technofine Co., Ltd.; top: polyurethane (blended with protein powder) 100%, base cloth: rayon 80% and nylon 20%) and was then dried for 24 hours at room temperature. A uniform, transparent and non-icky coat was formed on the surface of the artificial leather after being dried. After that, this artificial leather was stretched 110% in the cross direction and the surface state was observed to evaluate the coat properties. Namely, while a flexible coat maintains the surface state before stretching, even after stretching, a hard and fragile coat generates cracks or chaps on the surface. The evaluation standards are as follows and the mean values of five test results were obtained. 5: 80% or more of the surface remains unchanged from the state before stretching and exhibited flexible coat properties.

4: 60% or more and less than 80% of the surface remains unchanged from the state before stretching and exhibited flexible coat properties.

3: 40% or more and less than 60% of the surface remains unchanged from the state before stretching, and exhibited flexible coat properties.

2: 20% or more and less than 40% of the surface remains unchanged from the state before stretching, and exhibited flexible coat properties.

1: less than 20% of the surface remains unchanged from the state before stretching, and exhibited flexible coat properties.

Further, similar tests were performed on silicone resins A-2 to A-4 and B-1 to B-3 and evaluated. These results are shown in Table 1.

TABLE 1

Evaluation of Coat Properties

| Silicone resin | Evaluation score |
|---|---|
| A-1 | 4.6 |
| A-2 | 4.8 |
| A-3 | 4.4 |
| A-4 | 4.4 |
| B-1 | 3.0 |
| B-2 | 2.2 |
| B-3 | 2.6 |

The skin care cosmetic products and makeup cosmetic products were prepared and evaluated by using the silicone resin described above.

Skin Care Cosmetic Product
Evaluation Method 20 special panelists evaluated spreadability in use, icky feeling and long-wearing capability. The evaluation standards are as follows:

Spreadability in Use

◉: 16 to 20 panelists rated the spreadability in use as excellent.
○: 11 to 15 panelists rated the spreadability in use as excellent.
Δ: 6 to 10 panelists rated the spreadability in use as excellent.
X: 0 to 5 panelists rated the spreadability in use as excellent.

Icky Feeling

◉: 16 to 20 panelists did not feel icky in use and felt refreshed, rating it as excellent.
○: 11 to 15 panelists did not feel icky in use and felt refreshed, rating it as excellent.
Δ: 6 to 10 panelists did not feel icky in use and felt refreshed, rating it as excellent.
X: 0 to 5 panelists did not feel icky in use and felt refreshed, rating it as excellent.

Long-Wearing Capability

◉: 16 to 20 panelists rated the long-wearing capability as excellent.
○: 11 to 15 panelists rated the long-wearing capability as excellent.
Δ: 6 to 10 panelists rated the long-wearing capability as excellent.
X: 0 to 5 panelists rated the long-wearing capability as excellent.

Examples 1 to 4 and Comparative Examples 1 to 3

Hand Moisturizing Lotion (Production Method) (1) to (3) were mixed while stirring at 70 to 80° C., and a solution of (4) in which (5) was dissolved was added to this little by little and emulsified. Finally (6) was added therein to obtain a hand moisturizing lotion. The results were shown in Table 2.

TABLE 2

Hand moisture lotion

| Materials | Examples | | | | Comparative Examples | | |
|---|---|---|---|---|---|---|---|
| | 1 | 2 | 3 | 4 | 1 | 2 | 3 |
| (1) Decamethylcyclopentasiloxane | 30.0 | 30.0 | 30.0 | 30.0 | 30.0 | 30.0 | 30.0 |
| (2) Silicone resin A-1 | 40.0 | | | | | | |
| Silicone resin A-2 | | 40.0 | | | | | |
| Silicone resin A-3 | | | 40.0 | | | | |
| Silicone resin A-4 | | | | 40.0 | | | |
| Silicone resin B-1 | | | | | 40.0 | | |
| Silicone resin B-2 | | | | | | 40.0 | |
| Silicone resin B-3 | | | | | | | 40.0 |
| (3) Sorbitan monooleate | 5.0 | 5.0 | 5.0 | 5.0 | 5.0 | 5.0 | 5.0 |
| (4) Water | 21.9 | 21.9 | 21.9 | 21.9 | 21.9 | 21.9 | 21.9 |
| (5) Dipropylene glycol | 3.0 | 3.0 | 3.0 | 3.0 | 3.0 | 3.0 | 3.0 |
| (6) Flavor | 0.1 | 0.1 | 0.1 | 0.1 | 0.1 | 0.1 | 0.1 |
| Evaluation | | | | | | | |
| Spreadability in use | ◉ | ◉ | ○ | ◉ | ○ | Δ | Δ |
| Icky feeling in use | ◉ | ○ | ◉ | ○ | Δ | ○ | Δ |
| Long-wearing capability | ◉ | ◉ | ◉ | ◉ | X | Δ | Δ |

Example 5

Hand Cream (1) microcrystalline wax 3.0 parts (2) hard paraffin 2.0 parts (3) beeswax 3.0 parts (4) reduced lanolin 5.0 parts (5) flow paraffin 15.0 parts (6) spherical microparticle of methylpolysilsesquioxane resin (an average particle size 4.5 u) 5.0 parts (7) silicone resin A-1 45.0 parts (8) methylphenylsilicone oil 2.0 parts
(TSF4 37 from Momentive)

(9) decamethylcyclopentasiloxane 20.0 parts (Production Method) (1) to (9) were mixed while stirring at 70 to 80° C., which was further well dispersed by a homomixer to obtain a hand cream.

(Evaluation) The evaluation described above was conducted on the hand cream obtained. Spreadability in use was rated as ◉, icky feeling as ◉ and long-wearing capability as ◉.

Example 6

Hand Lotion (1) decamethylcyclotetrasiloxane 94.0 parts
(2) silicone resin A-2 2.8 parts
(3) silicone resin A-3 3.0 parts
(4) dimethylpolysiloxane 0.2 part
(Viscosity 20 million cP)

(Production Method) (1) to (4) were mixed while stirring at 70 to 80° C. to obtain a hand lotion.

(Evaluation) The evaluation described above was conducted on the hand lotion obtained. Spreadability in use was rated as ◉, icky feeling as ◉ and long-wearing capability as ◉.

Example 7

Sunscreen Cream (1) decamethylcyclopentasiloxane 13.0 parts
(2) silicone resin A-4 25.0 parts
(3) dimethylpolysiloxane (viscosity 6 cSt) 0.5 part
(4) liquid paraffin 0.5 part
(5) 4-methoxy-4-t-butyldibenzoylmethane 1.5 parts
(6) Polyether-modified Silicones 4.0 parts
(SF1118A from Momentive)
(7) water 40.1 parts
(8) sodium L-glutamate 3.0 parts
(9) 1,3-butylene glycol 5.0 parts
(10) 2-ethylhexyl-p-methoxycinnamate 7.0 parts
(11) antiseptic 0.2 part
(12) flavor 0.2 part (Production Method) (1) to (6) and (10), (11), (12) were dissolved at 70 to 80° C. to obtain an oil part. (8) and (9) were dissolved into (7) to make an aqueous phase part. The aqueous phase part was added to the oil part to be emulsified, which was further uniformly mixed by a homomixer to obtain the present article.

(Evaluation) The evaluation described above was conducted on the hand lotion obtained. Spreadability in use was rated as ◉, icky feeling as ◉ and long-wearing capability as ◉.

Makeup Cosmetic Product
Evaluation Method 20 special panelists evaluated spreadability in use, icky feeling and long-wearing capability. Evaluation standards are as follows:

Spreadability in Use
◉: 16 to 20 panelists rated the spreadability in use as excellent.
○: 11 to 15 panelists rated the spreadability in use as excellent.
Δ: 6 to 10 panelists rated the spreadability in use as excellent.
X: 0 to 5 panelists rated the spreadability in use as excellent.

Icky Feeling
◉: 16 to 20 panelists did not feel icky in use and felt refreshed, rating it as excellent.
○: 11 to 15 panelists did not feel icky in use and felt refreshed, rating it as excellent.
Δ: 6 to 10 panelists did not feel icky in use and felt refreshed, rating it as excellent.
X: 0 to 5 panelists did not feel icky in use and felt refreshed, rating it as excellent.

Long-Wearing Capability
◉: 16 to 20 panelists rated the long-wearing capability as excellent.
○: 11 to 15 panelists rated the long-wearing capability as excellent.
Δ: 6-10 panelists rated the long-wearing capability as excellent.
X: 0 to 5 panelists rated the long-wearing capability as excellent.

Finish Property
◉: 16 to 20 panelists perceived the finish as uniform and fine, rating it excellent.
○: 11 to 15 panelists perceived the finish as uniform and fine, rating it excellent.
Δ: 6 to 10 panelists perceived the finish as uniform and fine, rating it excellent.
X: 0 to 5 panelists o perceived the finish as uniform and fine, rating it excellent.

Examples 8 to 11, Comparative Examples 4 to 6

Mascara (Production Method) All except (4) were mixed while stirring at 70 to 80° C. (4) was added to this, sufficiently mixed and dispersed to obtain the present article. The results were shown in Table 3.

TABLE 3

| | Mascara | | | | | | |
|---|---|---|---|---|---|---|---|
| | Examples | | | | Comparative Examples | | |
| Materials | 8 | 9 | 10 | 11 | 4 | 5 | 6 |
| (1) Dimethylpolysiloxane | 1.5 | 1.5 | 1.5 | 1.5 | 1.5 | 1.5 | 1.5 |
| (2) Isododecane | 40.2 | 40.2 | 40.2 | 40.2 | 40.2 | 40.2 | 40.2 |
| (3) Silicone resin A-1 | 35.0 | | | | | | |
| Silicone resin A-2 | | 35.0 | | | | | |
| Silicone resin A-3 | | | 35.0 | | | | |
| Silicone resin A-4 | | | | 35.0 | | | |
| Silicone resin B-1 | | | | | 35.0 | | |
| Silicone resin B-2 | | | | | | 35.0 | |
| Silicone resin B-3 | | | | | | | 35.0 |
| (4) Iron oxide (black) | 20.0 | 20.0 | 20.0 | 20.0 | 20.0 | 20.0 | 20.0 |
| (5) POE(20) Sorbitan monolaurate | 3.0 | 3.0 | 3.0 | 3.0 | 3.0 | 3.0 | 3.0 |
| (6) Flavor | 0.3 | 0.3 | 0.3 | 0.3 | 0.3 | 0.3 | 0.3 |
| Evaluation | | | | | | | |
| Spreadability in use | ◉ | ○ | ◉ | ◉ | ○ | Δ | X |
| Icky feeling in use | ◉ | ◉ | ○ | ◉ | X | Δ | Δ |
| Long-wearing capability | ◉ | ◉ | ◉ | ◉ | X | Δ | Δ |
| Finish Property | ◉ | ◉ | ◉ | ◉ | X | Δ | Δ |

Examples 12 to 15, Comparative Examples 7 to 9

Oily Foundation (Production Method) The oily components of (8) to (16) were heat-dissolved at 70 to 80° C. and (7) was added therein to obtain an oil part. The powder components of (1) to (6) were added to the oil part and dispersed to obtain the present article. The results were shown in Table 4.

TABLE 4

Oily Foundation

| | | Examples | | | | Comparative Examples | | |
|---|---|---|---|---|---|---|---|---|
| | Materials | 12 | 13 | 14 | 15 | 7 | 8 | 9 |
| (1) | Talc | 10.0 | 10.0 | 10.0 | 10.0 | 10.0 | 10.0 | 10.0 |
| (2) | Mica | 7.0 | 7.0 | 7.0 | 7.0 | 7.0 | 7.0 | 7.0 |
| (3) | Titanium oxide | 15.0 | 15.0 | 15.0 | 15.0 | 15.0 | 15.0 | 15.0 |
| (4) | Iron oxide (yellow) | 0.4 | 0.4 | 0.4 | 0.4 | 0.4 | 0.4 | 0.4 |
| (5) | Iron oxide (red) | 0.25 | 0.25 | 0.25 | 0.25 | 0.25 | 0.25 | 0.25 |
| (6) | Iron oxide (black) | 0.03 | 0.03 | 0.03 | 0.03 | 0.03 | 0.03 | 0.03 |
| (7) | Light isoparaffin | 35.0 | 35.0 | 35.0 | 35.0 | 35.0 | 35.0 | 35.0 |
| (8) | Hard paraffin | 4.0 | 4.0 | 4.0 | 4.0 | 4.0 | 4.0 | 4.0 |
| (9) | Beeswax | 1.0 | 1.0 | 1.0 | 1.0 | 1.0 | 1.0 | 1.0 |
| (10) | Carnauba wax | 1.0 | 1.0 | 1.0 | 1.0 | 1.0 | 1.0 | 1.0 |
| (11) | Silicone resin A-1 | 20.0 | | | | | | |
| | Silicone resin A-2 | | 20.0 | | | | | |
| | Silicone resin A-3 | | | 20.0 | | | | |
| | Silicone resin A-4 | | | | 20.0 | | | |
| | Silicone resin B-1 | | | | | 20.0 | | |
| | Silicone resin B-2 | | | | | | 20.0 | |
| | Silicone resin B-3 | | | | | | | 20.0 |
| (12) | 2-Ethylhexyl-p-meth | 3.0 | 3.0 | 3.0 | 3.0 | 3.0 | 3.0 | 3.0 |
| (13) | Cetyl isooctanoate | 3.0 | 3.0 | 3.0 | 3.0 | 3.0 | 3.0 | 3.0 |
| (14) | Flavor | 0.3 | 0.3 | 0.3 | 0.3 | 0.3 | 0.3 | 0.3 |
| | Evaluation | | | | | | | |
| Spreadability in use | | ⊚ | ○ | ○ | ⊚ | ○ | Δ | X |
| Icky feeling in use | | ⊚ | ⊚ | ⊚ | ○ | X | Δ | Δ |
| Long-wearing capability | | ⊚ | ⊚ | ⊚ | ⊚ | Δ | Δ | Δ |
| Finish Property | | ⊚ | ⊚ | ⊚ | ⊚ | X | X | Δ |

Example 16

Pressed Powder Foundation (1) talk 20.0 parts
(2) mica 35.0 parts
(3) kaolin 2.0 parts
(4) titanium dioxide 12.0 parts
(5) mica titanium 3.0 parts
(6) zinc stearate 1.0 part
(7) iron oxide (red) 1.0 part
(8) iron oxide (yellow) 3.0 parts
(9) iron oxide (black) 0.2 part
(10) Silicone resin A-1 10.0 parts
(11) liquid paraffin 3.0 parts
(12) Light isoparaffin 2.0 parts
(13) 2-ethylhexyl-p-methoxycinnamate 7.0 parts
(14) antiseptic 0.2 part
(15) flavorant 0.3 part
(16) antioxidant 0.3 part (Production Method) The oily components of (10) to (16) were heat-dissolved at 70 to 80° C. to obtain an oil part. The powder components of (1) to (9) were well mixed, to which the oil part was added little by little, and further, mixed processing was performed to obtain the present article.

(Evaluation) The evaluation described above was conducted on the pressed powder foundation obtained. Spreadability in use was rated as ⊚, icky feel as ⊚, long-wearing capability as ⊚ and finish Property as ⊚.

Example 17

Makeup Base (1) silicone-treated kaolin 10.0 parts
(2) silicone-treated titanium dioxide 5.0 parts
(3) silicone-treated red iron oxide 0.3 part
(4) silicone-treated yellow iron oxide 0.2 part
(5) methylphenylpolysiloxane 2.0 parts
(TSF437 produced by Momentive)
(6) dimethylpolysiloxane (6 cSt) 2.0 parts
(7) hard paraffin 5.0 parts
(8) microcrystalline wax 4.0 parts
(9) sorbitan sesquioleate 1.2 parts
(10) silicone resin A-1 30.0 parts
(11) decamethylpentacyclosiloxane 34.0 parts
(12) 2-ethylhexyl-p-methoxycinnamate 6.0 parts
(13) flavorant 0.3 part (Production Method) The oily components of (5) to (13) were heat-dissolved at 70 to 80° C. to obtain an oil part. The powder components of (1) to (4) were added to the oil part and well dispersed, which was, after degassing, cooled to obtain the present article.

(Evaluation) The evaluation described above was conducted on the pressed powder foundation obtained. Spreadability in use was rated as ⊚, icky feeling as ⊚, long-wearing capability as ⊚ and finish Property as ⊚.

Example 18

Emulsified Eyeshadow (1) talc 10.0 parts
(2) kaolin 4.0 parts (3) pigment 5.0 parts
(4) silicone resin A-3 20.0 parts
(5) stearic acid 7.0 parts
(6) isopropyl myristate 1.0 part
(7) liquid paraffin 4.0 parts
(8) propylene glycol monolaurate 1.5 parts
(9) antioxidant 0.1 part
(10) flavorant 0.1 part
(11) water 40.2 parts
(12) 1,3-butyleneglycol 5.0 parts
(13) light isoparaffin 1.0 part
(14) antiseptic 0.1 part
(15) triethanolamine 1.0 part (Production Method) (4) to (10) and (14) were heat-dissolved at 60 to 70° C. and (13) was added therein to obtain an oil part. (12) and (15) were added to (11), further (1) to (3) were added, well dispersed and heated at 70 to 80° C. to make an aqueous phase part. The aqueous phase part was added to the oil part and emulsified, which was further emulsified by a homomixer to obtain the present article.

(Evaluation) The evaluation described above was conducted on the pressed powder foundation obtained. Spreadability in use was rated as ◉, icky feeling as ◉, long-wearing capability as ◉ and finish Property as ◉.

Example 19

Stick-Type Lip Rouge (1) paraffin wax 12.0 parts
(2) lanolin wax 10.0 parts
(3) kaolin 10.0 parts
(4) castor oil 40.0 parts
(5) decamethylcyclopentasiloxane 10.0 parts
(6) trioctanoic acid glyceride 3.0 parts
(7) candelilla wax 3.0 parts
(8) silicone resin A-1 8.0 parts
(9) titanium oxide 1.0 part
(10) Pigment Red 201 1.0 part
(11) Pigment Red 202 2.0 parts (Production Method) Those described above were heated for melting and uniformly mixed. This mixture was further homogeneously dispersed by a roller. The resulting mixture was degassed in a molten state to obtain a stick-type lip rouge.

(Evaluation) The evaluation described above was conducted on the stick-type lip rouge obtained. Spreadability in use was rated as ◉, icky feeling as ◉, long-wearing capability as ◉ and finish Property as ◉.

The invention claimed is:

1. A cosmetic product, comprising a silicone resin comprising (A) and (B) described below:

$$R_3SiO_{1/2} \text{ unit} \quad (A)$$

$$RSiO_{3/2} \text{ unit} \quad (B)$$

at a proportion of (A):(B) of 1:4.7 to 1:7 and having a softening point of 50 to 110° C., wherein R represents a substituted or unsubstituted monovalent hydrocarbon group.

2. The cosmetic product according to claim 1, wherein the molecular weight of the silicone resin is from 5,000 to 500,000.

3. The cosmetic product according to claim 1, wherein the silicone resin is produced by a first step of performing a hydrolysis and condensation reaction of an alkoxysilane represented by the formula (C) below and a second step of performing silylation with a chlorosilane represented by the formula (D):

$$RSi(OR')_3 \quad (C)$$

$$R_3SiCl \quad (D)$$

wherein R represents a substituted or unsubstituted monovalent hydrocarbon group and R' represents a substituted or unsubstituted hydrocarbon group having 1 to 6 carbon atoms.

4. The cosmetic product according to claim 3, wherein the first step of performing hydrolysis and condensation of the alkoxysilane is carried out in a solvent in an amount of 20 wt % or less.

5. The cosmetic product according to claim 1, wherein R is selected from the group consisting of an alkyl group, an alkenyl group, an aryl group, a cycloalkyl group and a halogen-substituted alkyl group.

6. The cosmetic product according to claim 1, wherein R is selected from the group consisting of an alkyl group and a halogen-substituted alkyl group.

7. The cosmetic product according to claim 1, wherein the silicone resin has a weight-average molecular weight of from 7,000 to 400,000.

8. The cosmetic product according to claim 1, additionally comprising another cosmetic material.

9. The cosmetic product according to claim 1, wherein the cosmetic product is a hand moisture lotion having an improved long-wearing capability.

10. The cosmetic product according to claim 1, wherein the cosmetic product is a mascara having an improved feeling during use, long-wearing capability and finish property.

* * * * *